US008241288B2

(12) United States Patent
Justin et al.

(10) Patent No.: US 8,241,288 B2
(45) Date of Patent: Aug. 14, 2012

(54) COLLET FIXATION SYSTEM

(75) Inventors: Daniel F. Justin, Logan, UT (US); Karen E. Mohr, Salt Lake City, UT (US); E. Marlowe Goble, Logan, UT (US)

(73) Assignee: IMDS Corporation, Logan, UT (US)

( * ) Notice: Subject to any disclaimer, the term of this patent is extended or adjusted under 35 U.S.C. 154(b) by 740 days.

(21) Appl. No.: 12/341,326

(22) Filed: Dec. 22, 2008

(65) Prior Publication Data
US 2009/0171357 A1 Jul. 2, 2009

Related U.S. Application Data

(60) Provisional application No. 61/015,374, filed on Dec. 20, 2007.

(51) Int. Cl.
*A61B 17/56* (2006.01)
(52) U.S. Cl. ........................................ 606/74
(58) Field of Classification Search .......... 606/103, 606/300, 139, 151, 263, 74; 24/129 A, 129 B, 24/130; 140/123.6, 93.2
See application file for complete search history.

(56) References Cited

U.S. PATENT DOCUMENTS

| 5,415,658 | A | * | 5/1995 | Kilpela et al. | ........ 606/300 |
| 5,649,927 | A | | 7/1997 | Kilpela | |
| 5,964,769 | A | * | 10/1999 | Wagner et al. | ........ 606/74 |
| 6,086,590 | A | | 7/2000 | Margulies | |
| 6,436,099 | B1 | * | 8/2002 | Drewry et al. | ........ 606/300 |
| 6,629,975 | B1 | | 10/2003 | Kilpela | |
| 6,730,092 | B2 | | 5/2004 | Songer | |
| 6,994,725 | B1 | * | 2/2006 | Goble | ........ 623/13.14 |
| 7,172,595 | B1 | | 2/2007 | Goble | |
| 2006/0235401 | A1 | | 10/2006 | Baldwin | |
| 2010/0179595 | A1 | | 7/2010 | Jackson | |

* cited by examiner

*Primary Examiner* — Thomas Barrett
*Assistant Examiner* — Melissa A Golob
(74) *Attorney, Agent, or Firm* — Peter K. Johnson; James Larson; G. So Hays

(57) ABSTRACT

A bone fixation assembly which may include a bone fixation element, a collet and a flexible line. The bone fixation element may comprise a first and second passageway and at least the first passageway is configured to receive the collet. The flexible line passes through both passageways and is secured through the second passageway. The collet may be advanced into the first passageway causing the collet to circumferentially engage the flexible line fixing it in place. Instrumentation for securing the collet includes a collet driver, a counter torque instrument and a tensioner.

30 Claims, 12 Drawing Sheets

US 8,241,288 B2

COLLET FIXATION SYSTEM

CROSS-REFERENCE TO RELATED APPLICATIONS

This application claims the benefit of the following, which is incorporated herein by reference:

Prior U.S. Provisional Patent Application No. 61/015,374, filed 20 Dec. 2007, and is entitled Collet Fixation System.

The following disclosure is incorporated herein by reference:

U.S. Pat. No. 7,172,595 B1, filed Jun. 2, 2005 and entitled BONE FIXATION SYSTEMS AND RELATED METHODS.

BACKGROUND OF THE INVENTION

1. The Field of the Invention

The present invention relates generally to the attachment of a bone fixation assembly to a bone, and more particularly, to cerclage wiring and to systems and methods for implanting fixation systems to secure bone fragments together or to secure prostheses to bone.

2. The Relevant Technology

Cerclage wiring is a technique in which surgeons tie pieces of bone together using metal wire or cable. This is commonly done in trauma cases to repair fractures and can include a variety of bones and parts of bones including patella, olecranon, femur, trochanter, tibia, etc. In some cases cerclage wiring has also been using in hip replacements—if the patient has poor bone stock in the femur, the surgeon may insert the implant into the femur and then tie cables and plates to the bone as well to help support the implant and keep it from breaking out of the bone. This is common known as periprosthetic cerclage.

One difficult aspect of cerclage wiring is providing retensioning of the wire or cable. In some cases the cable is passed through a cable receiving element and the cable and/or the cable receiving element is crimped or deformed in some manner to prevent withdrawal of the cable through the element. Although this method can be effective it may create a loosening of the cable when crimping. In addition the cable and the cable receiving element are irreversibly deformed disallowing retightening or adjustment.

Other techniques include a button or a pin attachment of the cable to a cable receiving element. Again, these may cause permanent deformity of the cable disallowing retightening or adjustment.

Other systems may also have set screws that are not in line with the cable and when the screws are tightened against the system the screws press against the cable. This system along with many other designs causes damage or deformation of the cable.

With either of these techniques a larger incision may be required because of the need for multiple instruments to tension the cable and crimp the cable, the element or both. Furthermore the inability to retighten the cables may result in a greater number of cables being used and a greater amount of time for surgery.

As the above described techniques illustrate, the existing systems and procedures for cerclage wiring may not be as effective as desired.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods for bone fixation elements and instrumentation for securing prosthetics to bone, fragments of bone together, bone to bone, tissue to bone or tissue to tissue. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

One embodiment of the present invention includes a bone fixation element with at least two passageways, a collet, a flexible line that passes through the collet and passageways, and bone fixation instrumentation. The instrumentation also comprises bores or passageways that allow the flexible line to pass through. The flexible line is preferably a polymer cord but may comprise a polymer cable, a metal cord or a metal wire, among others. A method of securing the bone fixation element includes securing one end of the flexible line to or within a first passageway, which may include a collet, of the bone fixation element and passing the line around the bone fragments and passing the flexible line through the bone fixation element through a second or separate passageway, which includes a collet. The flexible line passes through the collet and through the instrumentation. The flexible line may be tensioned with a tensioner as the collet advances into the bone fixation element causing the collet to circumferentially engage the flexible line securing the flexible line within the collet, which collet is within the bone fixation element. With circumferential engagement of the flexible line minimal deformation or damage occurs to the flexible line.

Figure 1:
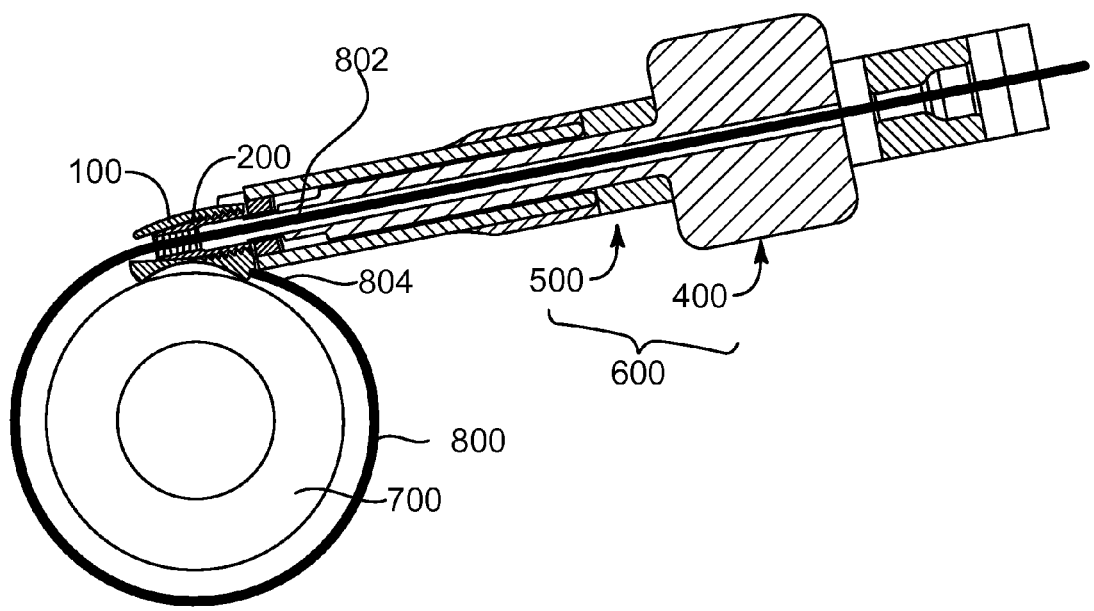
FIG. 1 illustrates a cross-sectional side view of a bone, a bone fixation assembly with a flexible line, a collet, a bone fixation element and a bone fixation instrument assembly with a collet driver and a counter torque instrument.

Referring to FIG. 1, a bone fixation instrument assembly 600 comprises a collet driver 400 and a counter torque instrument 500. The counter torque instrument 500 and the collet driver 400 are engaged with a bone fixation assembly comprising a bone fixation element 100 and a collet 200. A flexible line 800 comprises a first working portion 802 and a second working portion 804 connected to the first working portion 802. The flexible line 800 engages the bone fixation element 100 with the second working portion 804. The second working portion 800 is secured to the bone fixation element 100. The flexible line 800 wraps around bone fragments or a bone 700 and slidably passes through the collet 200, the bone fixation element 100, the collet driver 400, and the counter torque instrument 500. The first working portion 802 is secured to the bone fixation element 100 by advancing the collet 200 into the bone fixation element 100. The collet 200 circumferentially compresses around the first working portion 802, thus fixing it to the bone fixation element 100.

FIGS. 2-6 illustrate an embodiment of a bone fixation element with at least two passageways provided for a flexible line to pass through. The bone fixation elements described herein may comprise any biocompatible material including stainless steel, titanium, cobalt chrome, other metals or metal alloys, or polymers, including polyetheretherketone (PEEK), or any bioabsorbable materials.

Figure 2:
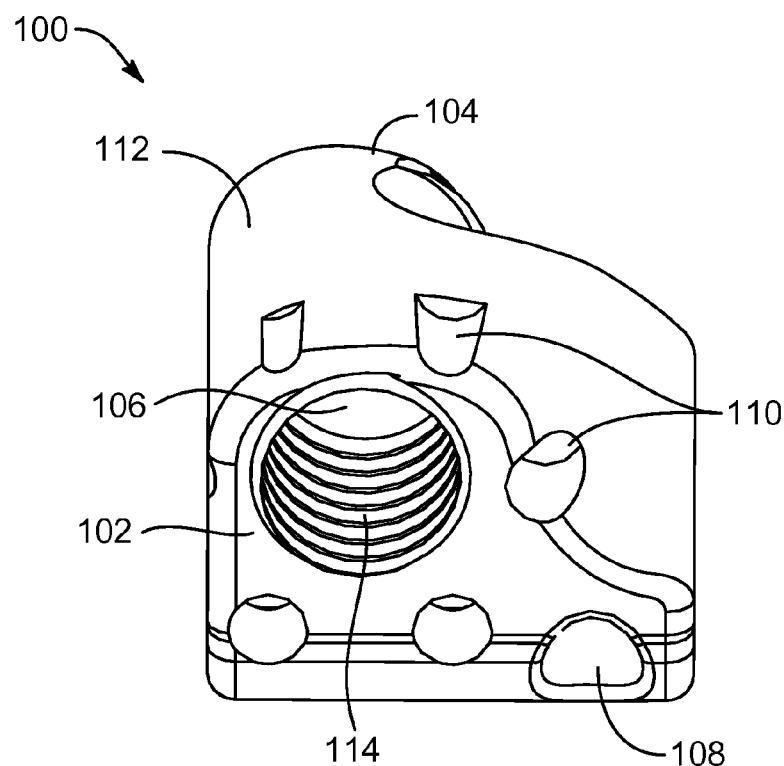
FIG. 2 illustrates a front perspective view of the bone fixation element of FIG. 1.

Referring to FIGS. 1 and 2, a bone fixation element 100 includes a first end 102, a second end 104 opposite the first end and a top portion 112 connecting the two ends 102, 104. A first passageway 106 traverses the bone fixation element from the first end 102 to the second end 104 and may include threads 114. The threads 114 may be used to secure the collet 200 within the first passageway 116. A second passageway 108, which may be separate from the first passageway 106, traverses the bone fixation element 100 from the second end 104 to the first end 102. The second passageway 108 may be radially smaller and longitudinally shorter than the first passageway 106. The passageways 106, 108 may be partially or fully enclosed. The first end 102 may include slots 110 which may be equally spaced around an opening for the first passageway 106. Each slot 110 is generally circular in shape; however each slot 110 may be any geometric shape providing an interface for the counter torque instrument 500 with a complimentary fit. The counter torque instrument 500 may be inserted into the slots 110 providing counter torque when collet 200 is advanced into the first passageway 106.

Figure 3:
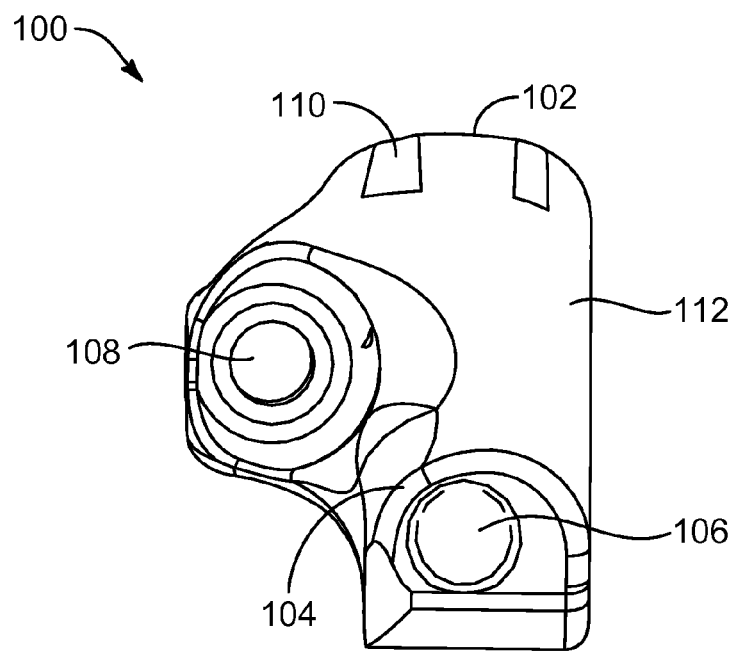
FIG. 3 illustrates a back perspective view of the bone fixation element of FIG. 1.

Referring to FIG. 3, the bone fixation element 100 is illustrated from the opposite viewpoint of FIG. 2. The second passageway 108 may slidably receive a flexible line 800.

Figure 4:
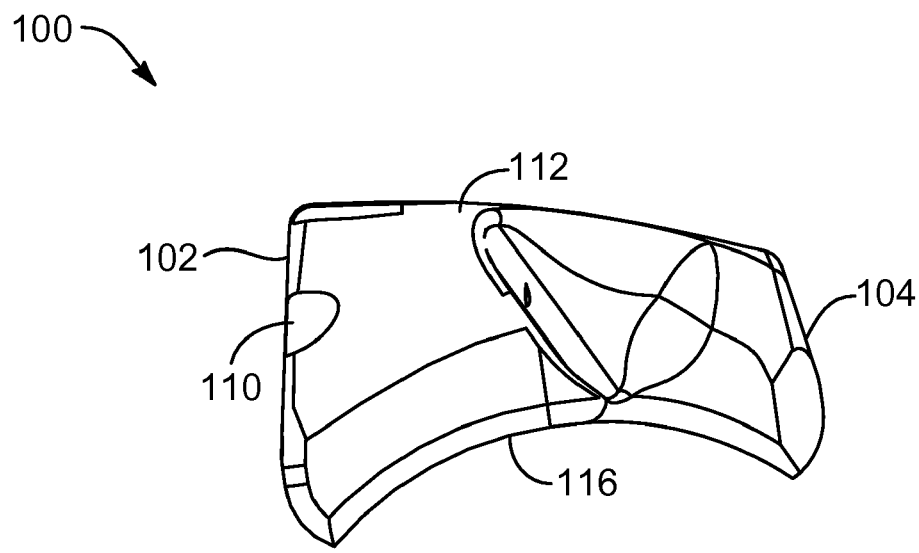
FIG. 4 illustrates a side view of the bone fixation element of FIG. 1; with a bone engagement surface, a top portion, a first end and a second end.

Referring to FIG. 4, the bone fixation element 100 includes a bone engagement surface 116 which may be concave. The concavity of the bone engagement surface 116 may compliment that of a bone (not shown) or bone fragments (not shown) on which the bone fixation element 100 is placed. The bone engagement surface 116 may include protrusions (not shown) extending from the surface including, but not limited to, ridges, prongs or teeth which may aid in securing the bone fixation element to the bone.

Figure 5:
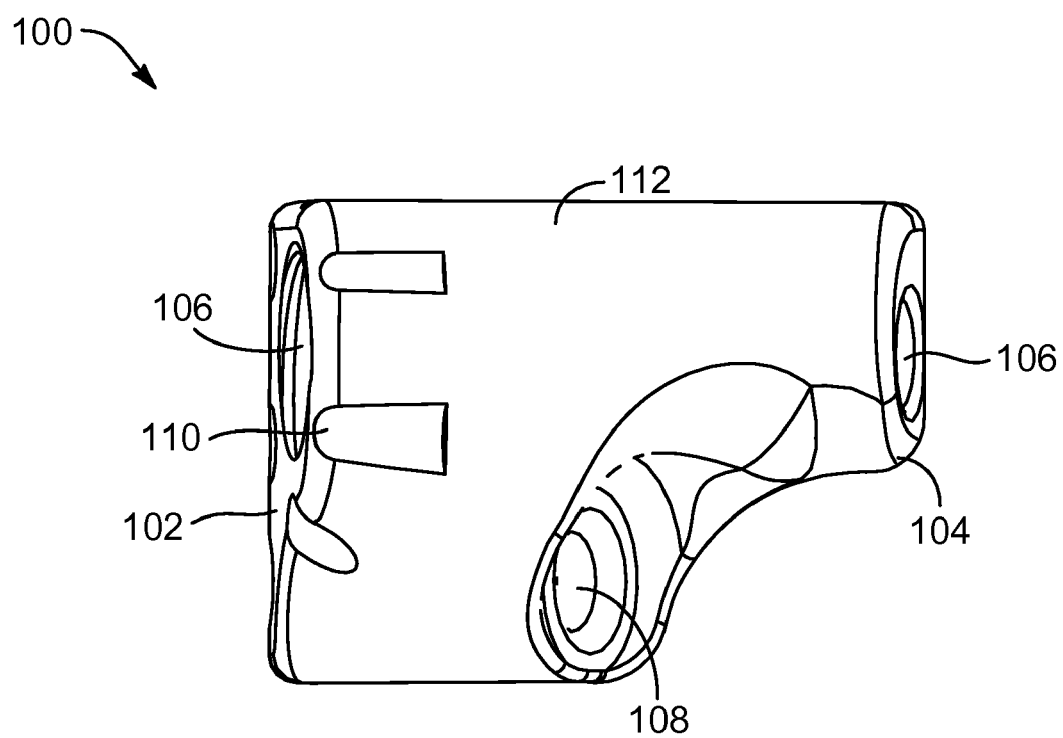
FIG. 5 illustrates a top view of the bone fixation element of FIG. 1.
Figure 6:
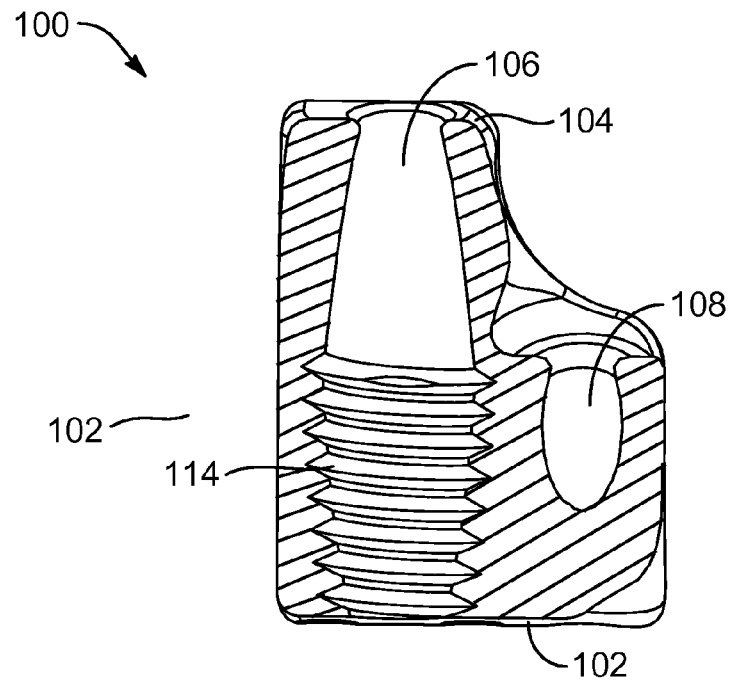
FIG. 6 illustrates a top cross-sectional view of the bone fixation element of FIG. 1.

Referring to FIGS. 1, 5 and 6, the distance between the first end 102 and the second end 104 of bone fixation element 100 may vary. The length of the first passageway 106 may be greater or less than the length of the second passageway 108. The first passageway 106 may taper when moving from the first end 102 to the second end 104 forcing the collet 200 to circumferentially compress and secure the first working portion 802 of the flexible line 800 within the collet. The threads 114 extending within the first passageway 106 from the first end 102 to the second end 104 may equal to or greater than the length of the complimentary collet threads, thus allowing the collet 200 to be completely inserted into the bone fixation element 100 without any part of the collet protruding. The second passageway 108 is configured to receive the second working portion 804 of the flexible line 800 as well and may be secured with a knot (not shown) tied in second working portion 804, preventing withdrawal of the flexible line 800 through the second passageway 108. It will be appreciated that any means known in the art may be used to prevent withdrawal of the flexible line 800 through the second passageway 108, including but not limited to crimps, pins, screws or buttons which may engage the line outside of and/or within the second passageway to prevent the withdrawal.

Other possible means for securing the collet 200 to the bone fixation element 100 may include a snap feature (not shown) with a first snap interface on the collet 200 and a second snap interface on the bone fixation element 100. The bone fixation element 100 may include multiple snap interfaces preventing withdrawal of the collet 200 thus allowing the collet 200 to slide further within the first passageway 106 by engaging each successive snap interface deeper within the first passageway 106 compressing the collet 200 further with each successive snap.

Figure 7:
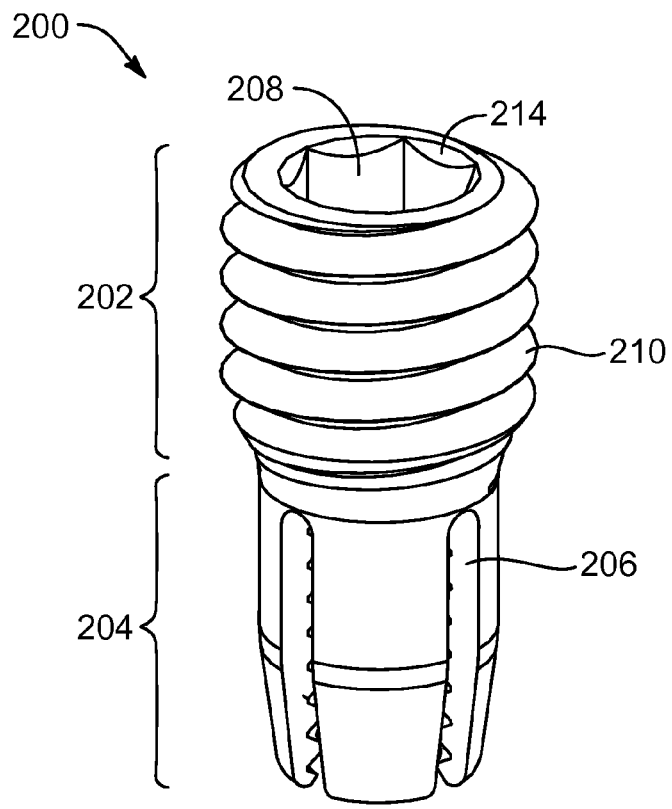
FIG. 7 illustrates a perspective view of the collet of FIG. 1.
Figure 8:
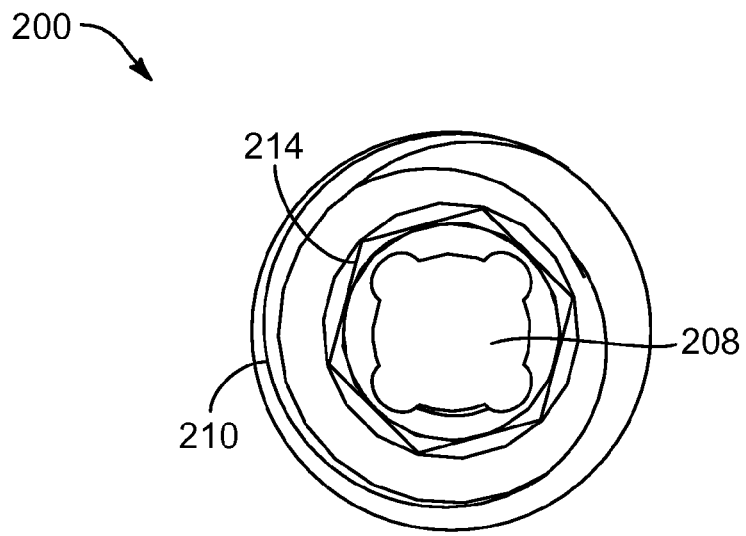
FIG. 8 illustrates a top view of the collet of FIG. 1.
Figure 9:
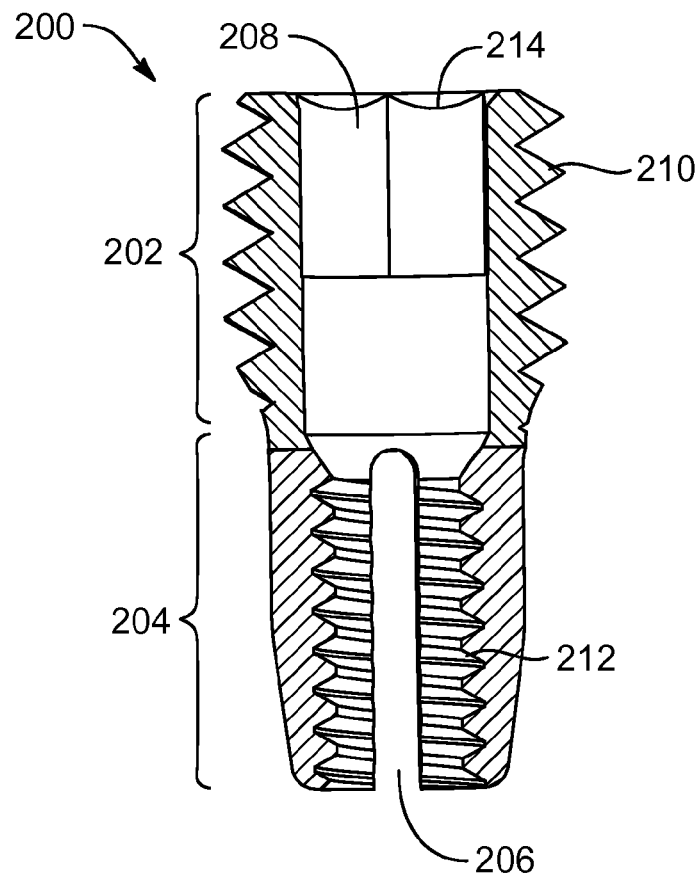
FIG. 9 illustrates side cross-sectional side view of the collet of FIG. 1.

FIGS. 7-9 illustrate an embodiment of a collet with a central bore and at least one slit. Referring to FIGS. 7 and 8, the collet 200 includes a first portion 202, a second portion 204 and a central bore 208 which extends longitudinally through the collet. The central bore 208 allows the passage of the flexible line 800 through the collet.

The first portion, or engagement portion, 202 may engage with the bone fixation element 100. The engagement portion 202 may comprise threads 210 or may comprise a snap feature (not shown) to enhance engagement with the bone fixation element. The threads 210 provide threadable engagement with the first passageway 106. A snap feature (not shown) on the collet 200 may be configured with a snap interface configured to interact with a snap feature of the bone fixation element 100. The first engagement portion 202 also includes a collet driver interface 214 providing a means for attachment of the collet driver 400. The collet driver interface 214 may be a hexagonal shape bore, which may be part of the central bore 208, allowing the collet driver 400 with a complimentary interface to be inserted into the central bore 208. The collet driver interface 214 need not be hexagonal in shape, but may be square, triangular or any shape which may engage with any instrument or other means known in the art for driving or advancing a collet or other like fastener.

Referring to FIG. 9, the second portion 204 may comprise at least one slit 206 allowing the second portion 204 to circumferentially compress when advanced into the first passageway 106. The second portion 204 may further comprise ridges 212 formed within the central bore 208. The ridges 212 may be any protrusion including threads, prongs or teeth. The ridges 212 may enhance the engagement between the collet 200 and the first working portion 802 of the flexible line 800.

The collet 200 may be tubular, cylindrical or conical or the like and also may taper or narrow toward one end of the collet, such that the diameter of one end of the collet is greater than a diameter at the opposite end. The collet may be comprised of any biocompatible material including stainless steel titanium, cobalt chrome, polymer, including polyetheretherketone (PEEK), or any bioabsorbable materials.

Figure 10:
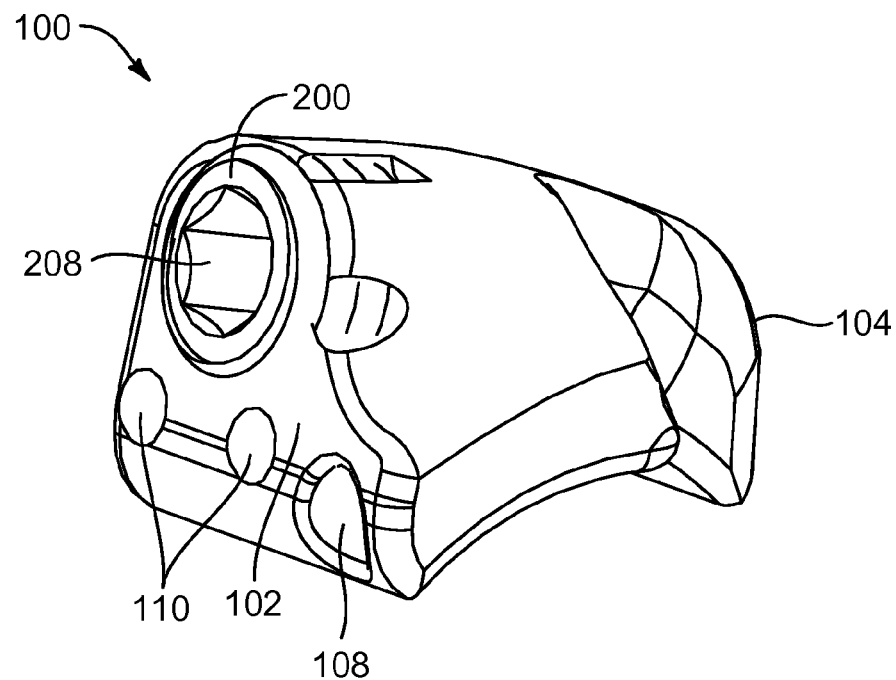
FIG. 10 illustrates a perspective view of the bone fixation element and collet of FIG. 1, the collet entirely within a first passageway.

Referring to FIG. 10, the collet 200 is shown in a first engaged position in which it is positioned entirely within the bone fixation element 100 to provide a flush surface with the first end 102. The collet 200 may also be further within the bone fixation element 100 such that the collet is advanced beyond being flush with the first end 102. The first engaged position of the collet 200 circumferentially engages the first working portion 802 of the flexible line 800 holding it in a fixed position.

Figure 11:
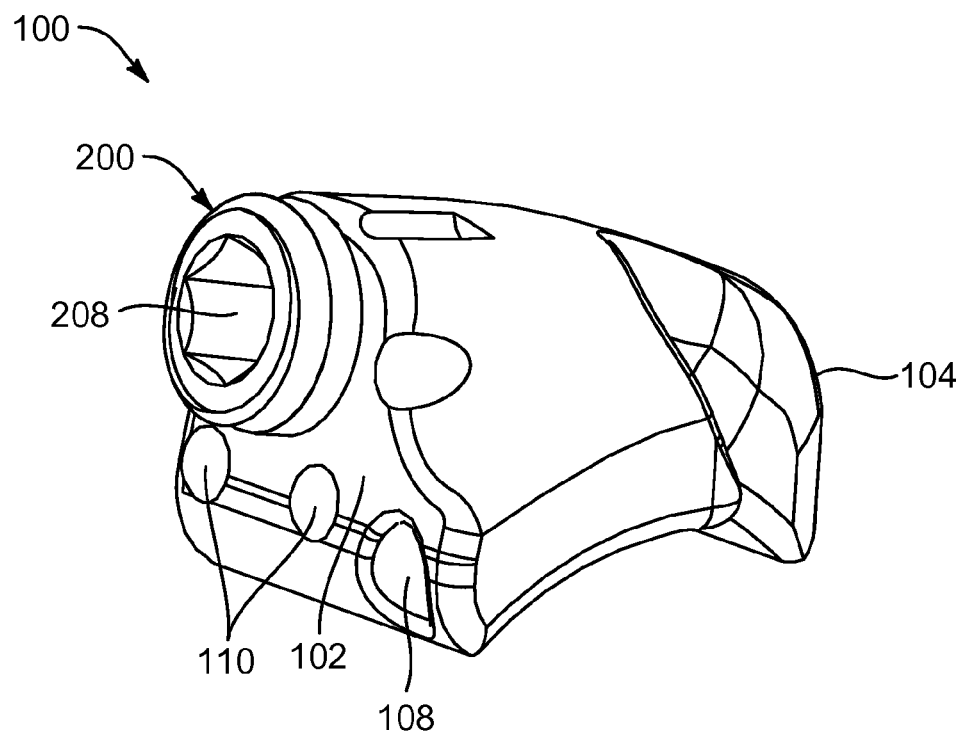
FIG. 11 illustrates a perspective view of the bone fixation element and collet of FIG. 1, the collet partially within the first passageway.

Referring to FIG. 11, the collet 200 is in a second position positioned at least partially within the bone fixation element 100. The second position allows the first working portion 802 of the flexible line 800 to slidably pass through the collet 200. However, another embodiment may provide for the collet to engage and lock the position of the flexible line while positioned only partially in the bone fixation element.

The threadable collet 200 in conjunction with the threadable bone fixation element 100 also allows for loosening of the collet 200 which allows for additional tensioning of the flexible line 800. The collet 200 can be loosened and retightened within the bone fixation element 100 disengaging and engaging and fixing the flexible line 800.

Furthermore the system of the flexible line 800, the bone fixation element 100 and the collet 200, with its circumferential engagement, maintains everything in line such that the first working portion of the flexible line, the collet and first passageway are co-axial. This line may also be true with the instrumentation including the counter torque instrument 500 and the collet driver 400.

Figure 12:
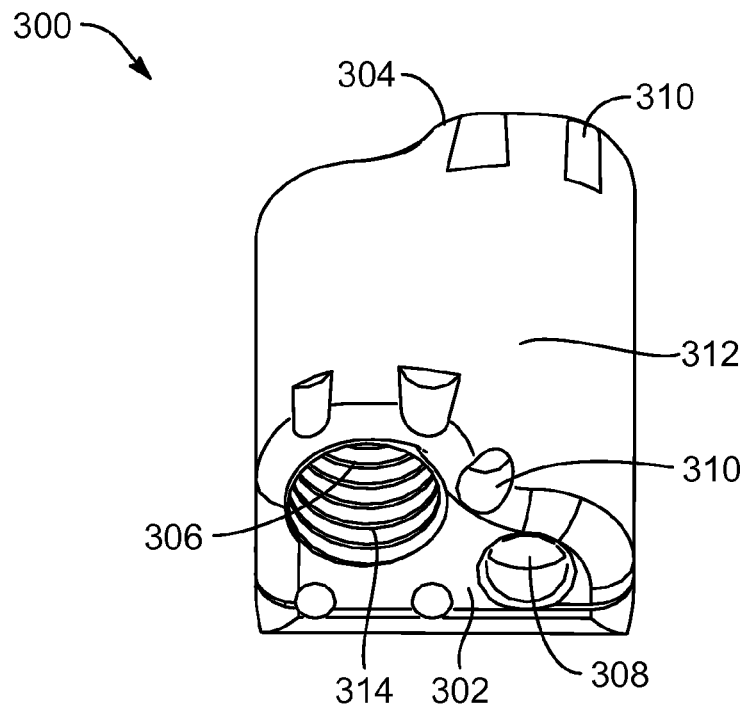
FIG. 12 illustrates a perspective view of a separate embodiment of a bone fixation element with a first end, a first passageway and a second passageway.

FIGS. 12-16 illustrate an alternate embodiment of a bone fixation element with at least two passageways, wherein two separate collets may be inserted, providing for a flexible line to pass through. Referring to FIG. 12, an alternate embodiment of a bone fixation element 300 includes first end 302, a top portion 312 and a second end 304. A first passageway 306 traverses the bone fixation element 300 from the first end 302 to the second end 304. A second passageway 308, which may be separate from the first passageway 306, traverses the bone fixation element 300 from the second end 304 to the first end 302. The first end 302 may include slots 310 which may be equally spaced around an opening for the first passageway 306. Each slot 310 as shown is generally circular in shape; however each slot 310 may be any geometric shape providing an interface for the counter torque instrument 500 with a complimentary fit. The counter torque instrument 500 may be inserted into the slots 310 providing counter torque when the collet 200 is inserted into a first passageway 306. The second end 304 may also include slots 310 with the same structure and function as those previously described. The first and second passageways 306, 308 may also include threads which extend at least partially through the first and second passageways 306, 308 from the first end 302 and second end 304 respectively.

Figure 13:
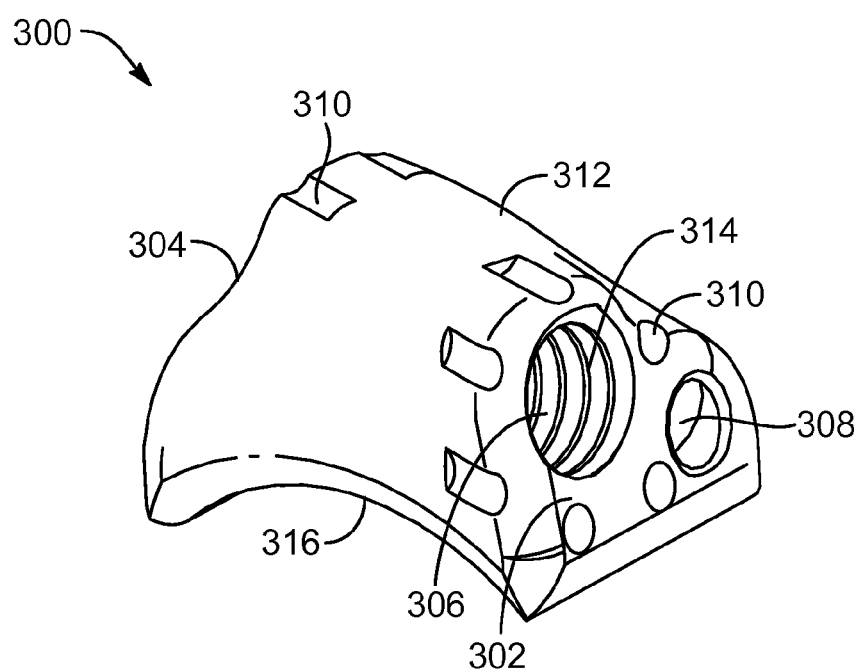
FIG. 13 illustrates a perspective view of the bone fixation device of FIG. 12.
Figure 14:
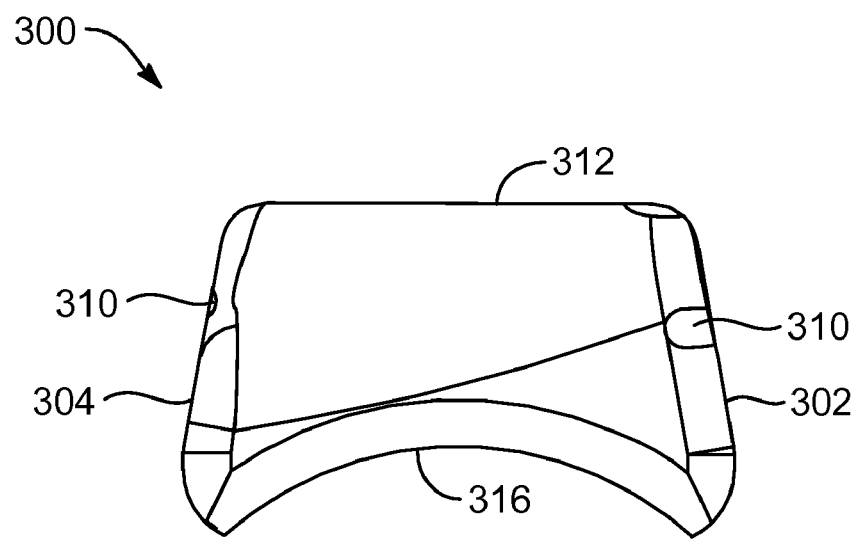
FIG. 14 illustrates a side view of the bone fixation device of FIG. 12.

Referring to FIGS. 13 and 14, the bone fixation element 300 includes a bone engagement surface 316 which may be concave. The concavity of the bone engagement surface 316 may compliment that of a bone (not shown) or bone fragments (not shown) on which the bone fixation element 300 is placed. The bone engagement surface 316 of this embodiment may also include protrusions (not shown) extending from the surface including, but not limited to, ridges, prongs or teeth which may aid in securing the bone fixation element to the bone.

Figure 15:
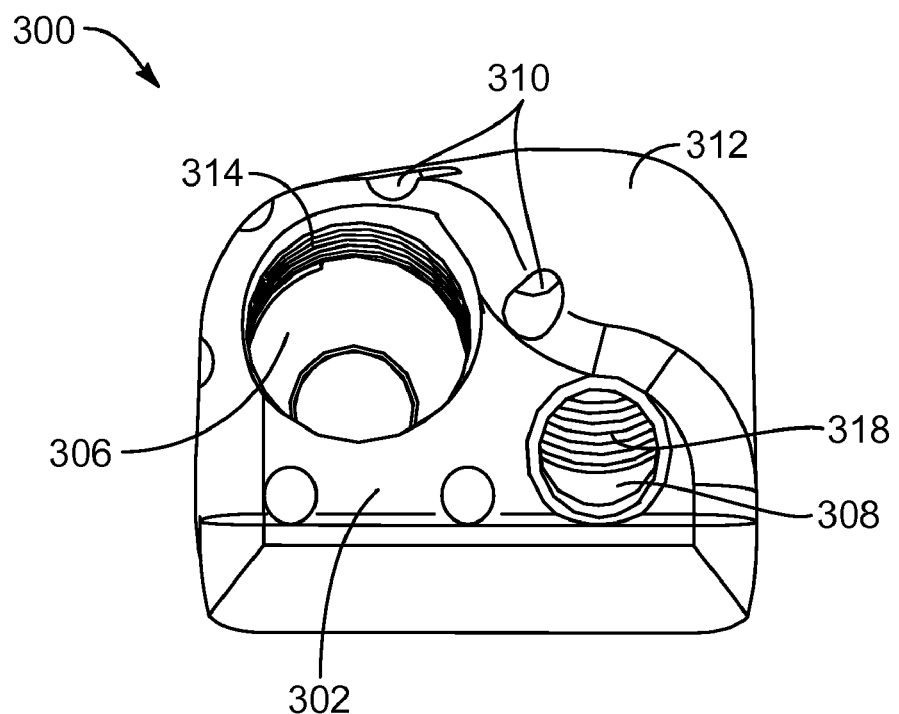
FIG. 15 illustrates a front view of the bone fixation device of FIG. 12.
Figure 16:
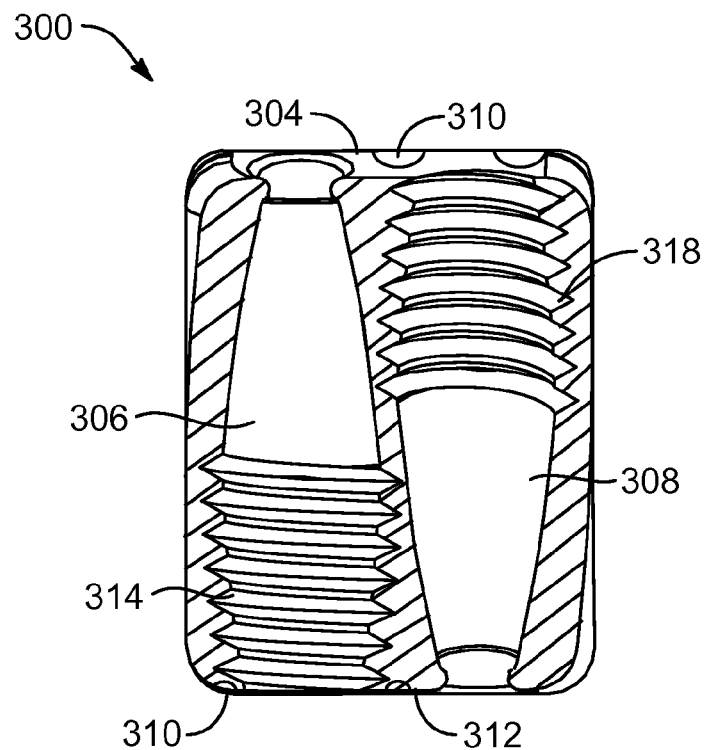
FIG. 16 illustrates a top cross-sectional view of the bone fixation device of FIG. 12.

Referring to FIGS. 15 and 16, the first passageway 306 may taper from the first end 302 to the second end 304. The taper forces the collet 200 to circumferentially compress as it is advanced into the passageway, securing the first working portion 802 of the flexible line 800 within the collet 200. Threads 314 may extend within the first passageway 306 from the first end 302 to the second end 304 to a length equal to or greater than the length of the complimentary collet threads 210, thus allowing the collet 200 to be inserted entirely into the first passageway 306 without any part of the collet 200 protruding (such as in FIG. 10). The second passageway 308 may taper from the second end 304 to the first end 302 forcing a second collet 200 to circumferentially compress and secure the second working portion 804 of the flexible line 800 within the second collet 200. Threads 314 may extend within the second passageway 308 from the second end 304 to the first end 302 to a length equal to or greater than the length of the complimentary collet threads 210 similar to the first passageway 306, allowing the collet 200 to be inserted entirely into the second passageway 308 without any part of the collet 200 protruding (such as in FIG. 10).

Other possible means for securing each of the collets 200 to the bone fixation element 300 may include a snap feature (not shown) with a first snap interface on the collet and a second snap interface on the bone fixation element 300. The bone fixation element 300 may include multiple snap interfaces preventing withdrawal of the collet 200 thus allowing the collet 200 to slide further within the first and second passageways 306, 308 by engaging each successive snap interface deeper within the passageways 306, 308, collapsing the collet 200 further with each successive snap.

Figure 17:
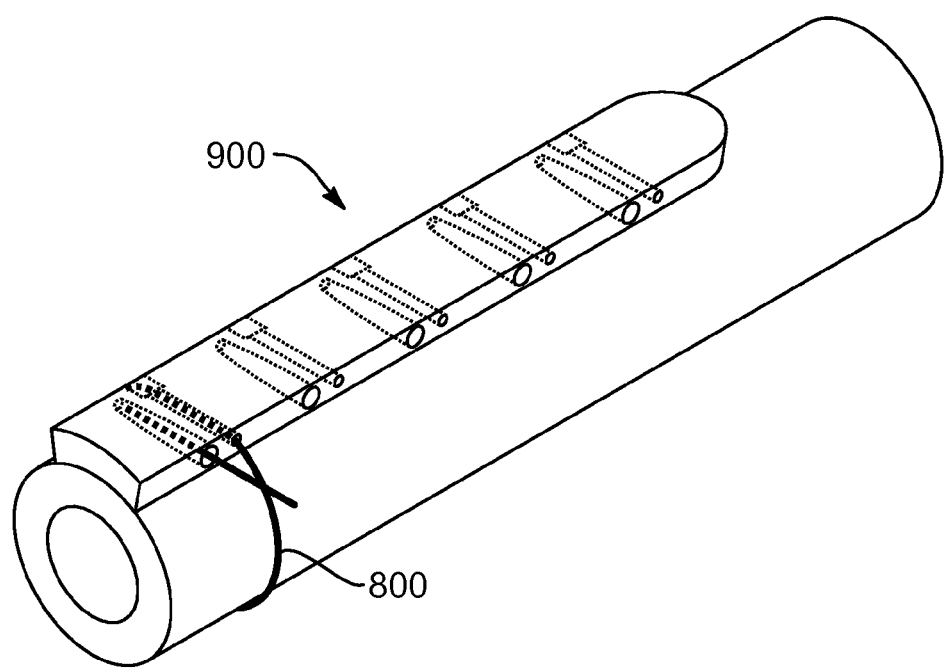
FIG. 17 illustrates a perspective view of a bone plate fixation element with multiple passageways.

Referring to FIG. 17, an alternate embodiment of the bone fixation element is a bone plate fixation element 900, similar to a bone plate, which may include two or more passageways. This alternate embodiment may comprise multiple passageways, at least one of such passageways configured to engage at least one collet 200. The method for flexible line 800 engagement is be the same or similar to the bone fixation element 100 and 300 embodiments, but using multiple flexible lines, or a single flexible line extending through multiple passageways, secured by at least one collet. The bone plate fixation element 900 may also include components similar to those found on the previously disclosed embodiments such counter torque slots and a concave bone interface surface which may include protrusions.

Any of the possible embodiments of the bone fixation element may comprise any biocompatible material including stainless steel, titanium, cobalt chrome, polymer, including polyetheretherketone (PEEK), or any bioabsorbable materials.

Figure 18:
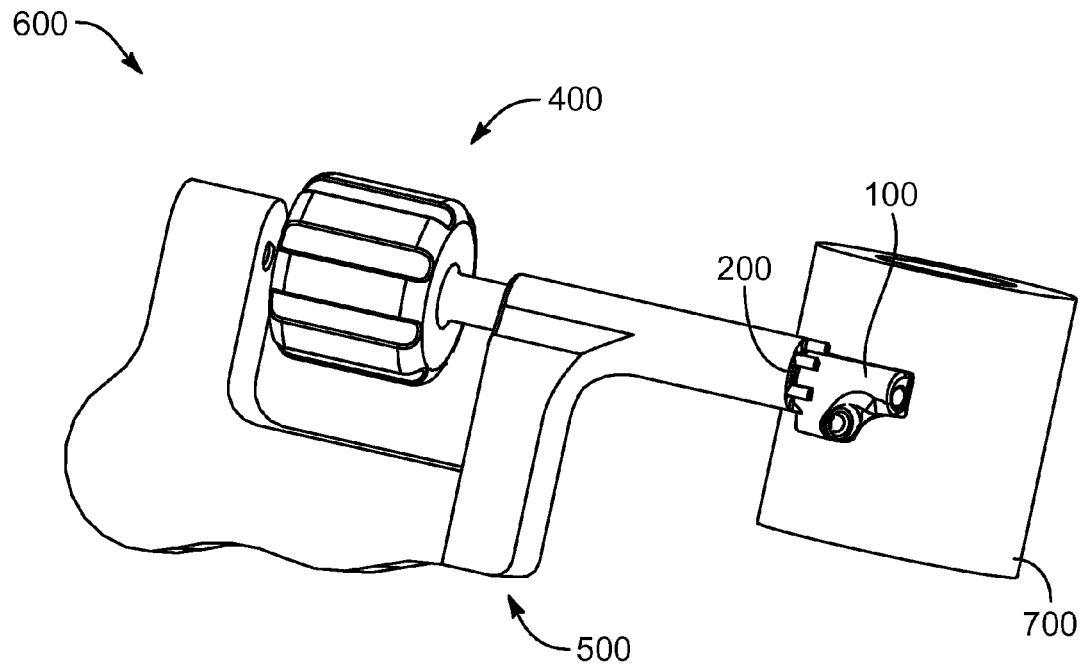
FIG. 18 illustrates a perspective view of the bone fixation element and the bone fixation instrument assembly of FIG. 1, and a bone.

FIGS. 18-23 illustrate a bone fixation assembly system with a counter torque instrument, a collet driver, a collet, a bone fixation element and a cable. Referring to FIG. 18, a bone fixation instrument assembly 600 includes a collet driver 400 and a counter torque instrument 500. Bone fixation instrument assembly 600 is suitable for use with the bone fixation elements disclosed herein, or with a similar device.

Figure 19:
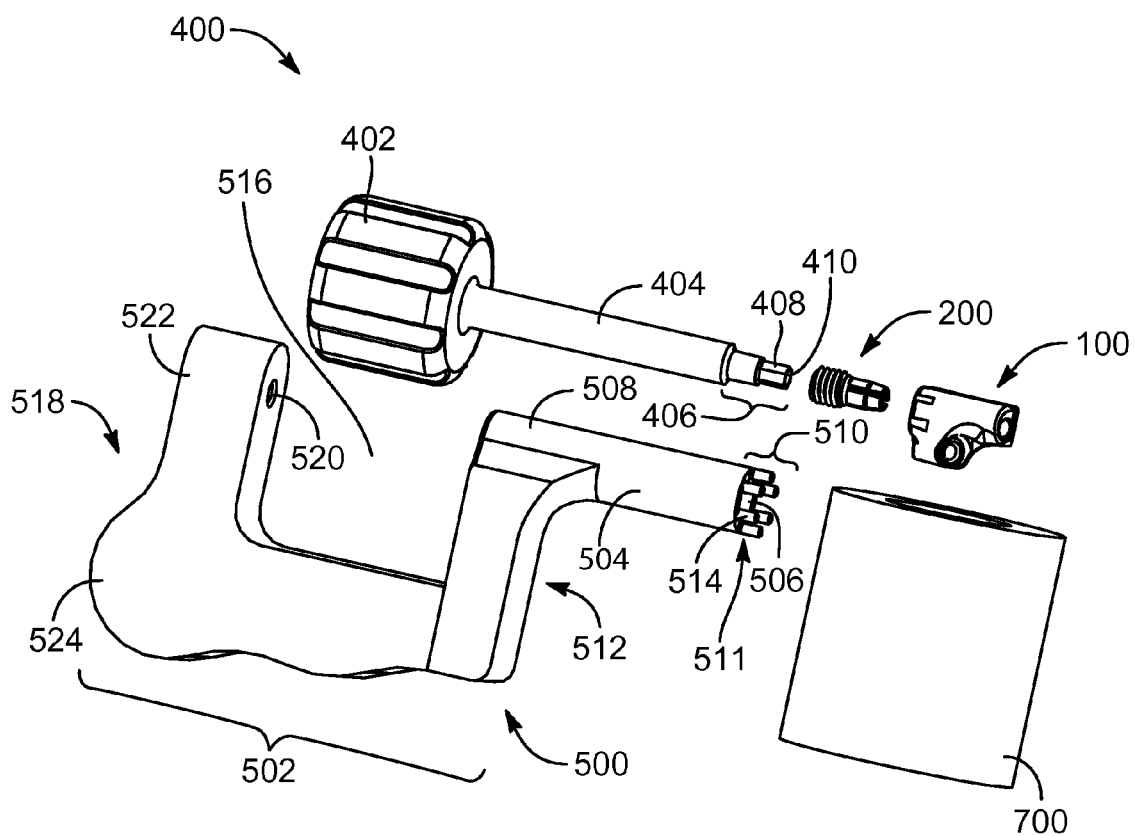
FIG. 19 illustrates an exploded perspective view of the bone fixation instrument assembly and bone fixation assembly of FIG. 1.

Referring to FIG. 19, the collet driver 400 includes a proximal handle portion 402, a distal portion 406, and a collet driver shaft 404 extending between the proximal handle portion 402 and the distal portion 406. The proximal handle portion 402 may be radially larger than the collet driver shaft 404 and the collet driver shaft 404 may be radially larger than the distal portion 406. The proximal handle portion 402 may have ridges or grips which allow for easier manipulation of the collet driver 400. The distal portion 406 includes a collet engagement interface 408 which is slidably insertable into the collet 200 to engage the collet driver interface 214. Like the collet driver interface 214 the collet engagement surface 408 may be any shape that compliments the collet driver interface 214.

The collet driver 400 also includes a collet driver bore 410 which extends longitudinally through the collet driver 400. The collet driver bore 410 is large enough to slidably receive the flexible line 800 (not shown) which has been routed around the bone 700 or bone fragments (not shown) through the bone fixation element 100 and the collet 200.

The counter torque instrument 500 includes a counter torque handle 502 and a counter torque shaft 504. The counter torque shaft 504 is positioned distal the counter handle 502 and a first arm 512 of the counter torque handle 502 extends non-parallel to the counter torque shaft 504. The counter torque shaft 504 includes a shaft proximal portion 508 whereat the first arm 512 may engage the counter torque shaft 504. The counter torque shaft may also comprise a shaft distal portion 510. At the distal end of the shaft distal portion 510 there is a key 511 which may be comprised of prongs 514 extending parallel to the counter torque shaft 504. The prongs 514 are configured to slidably engage the slots 110 of the bone fixation element 100, and thus may be circular as shown or any other shape complementing the slots 110. The engagement of the key 511 provides counter torque to the collet driver 400 as the driver is rotated to advance or remove a collet.

Figure 20:
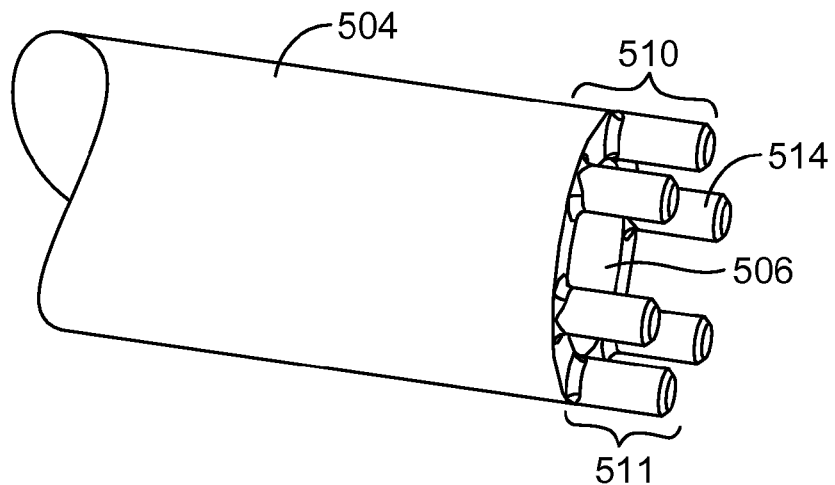
FIG. 20 illustrates a blown up perspective view of a distal portion of the counter torque shaft of FIG. 1.

FIG. 20 provides a larger view of the of the counter torque shaft 504 showing more detail regarding the shaft distal portion 510 comprising the key 511 comprising prongs 514. The prongs 514 may also engage the bone fixation element 100 by alternate means including forcible engagement or snap fit engagement.

Figure 21:
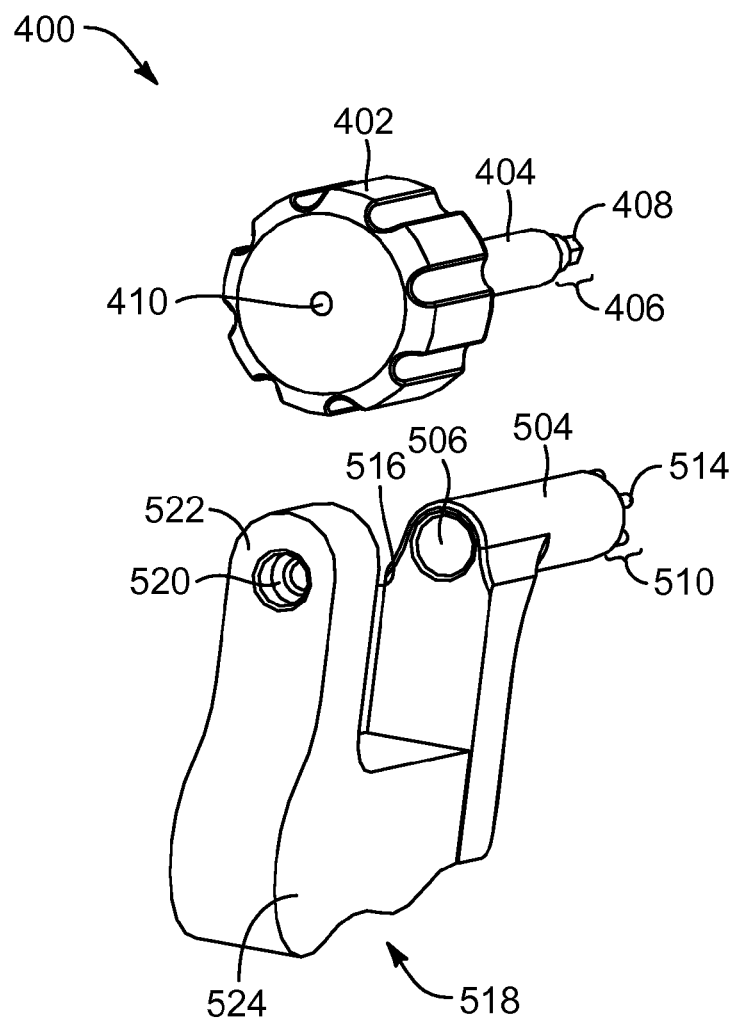
FIG. 21 illustrates a slightly back exploded perspective view of the bone fixation instrument assembly of FIG. 1.

Referring to FIGS. 19 and 21, the counter torque shaft 504 further comprises an outer wall defining a shaft bore 506 that is large enough to slidably retain the collet driver shaft 404. The collet driver 400 is able to be manipulated within the shaft bore 506 allowing the collet driver 400 to rotate independent from but coaxial with the shaft bore 506.

The counter torque handle 502 may further comprise a second arm 518 extending non-parallel to the first arm 512. The second arm 518 may comprise an elbow 524 and a handle distal portion 522. The handle distal portion 522 of the second arm 518 comprises a second arm bore 520. The second arm bore 520 is coaxial with the shaft bore 506. The second arm bore 520 may be radially smaller at its distal end than at its proximal end. The counter torque handle 502 may further comprise a notch 516 between the shaft bore 506 and the second arm bore 520. With the first arm 512 and second arm 518, the counter torque handle 502 may resemble a "C" or a "U" shape. The counter torque handle 502 is positioned such that the proximal handle portion 402 of the collet driver 400 may reside in the notch 516.

The second arm bore 520 is configured to slidably receive a tensioner (not shown) at least partially within the proximal end of the second arm bore 520. The tensioner is configured to receive the flexible line 800 and provide tension control to the flexible line 800. Actuation of the tensioner engages the flexible line 800 to provide tension to the flexible line 800. The tensioner may be any type of instrument known in the art configured to tension a flexible line or cable.

Other means of tensioner engagement to the counter torque handle 502 may include forcible insertion into the second arm bore 520, or the second arm bore 520 may comprise threads wherein the tensioner may be threadably inserted into the second arm bore 520.

Figure 22:
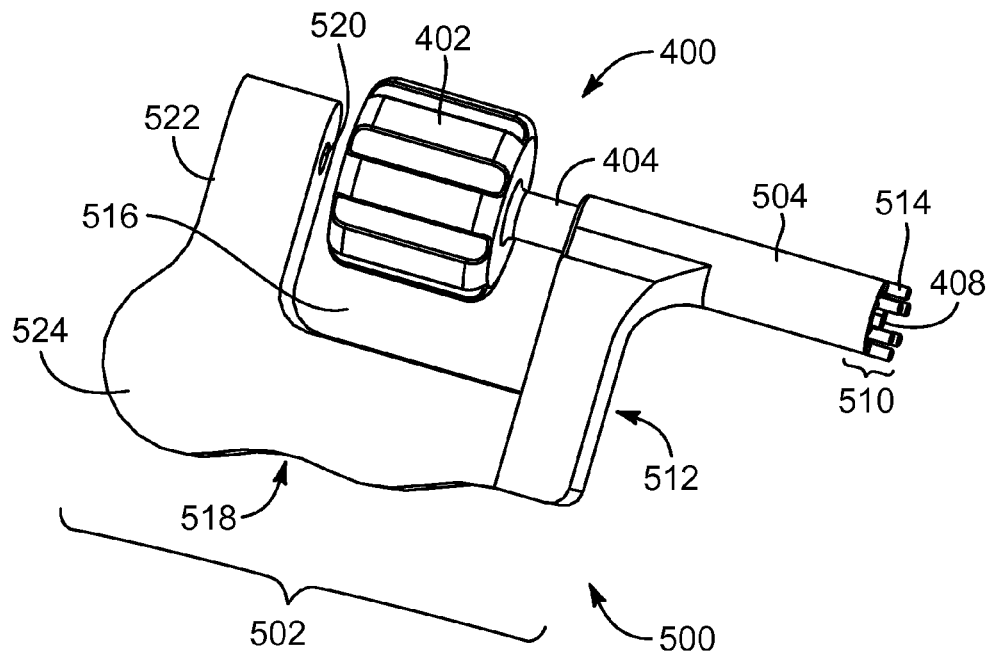
FIG. 22 illustrates a perspective view of a bone fixation instrument assembly of FIG. 1.

Referring to FIG. 22, the second arm bore 520 is further coaxially aligned with the collet driver bore 410 wherein the collet driver 400 is positioned within the counter torque shaft 504. The alignment of each bore provides slidably passage of the flexible line 800 (see FIG. 1).

Figure 23:
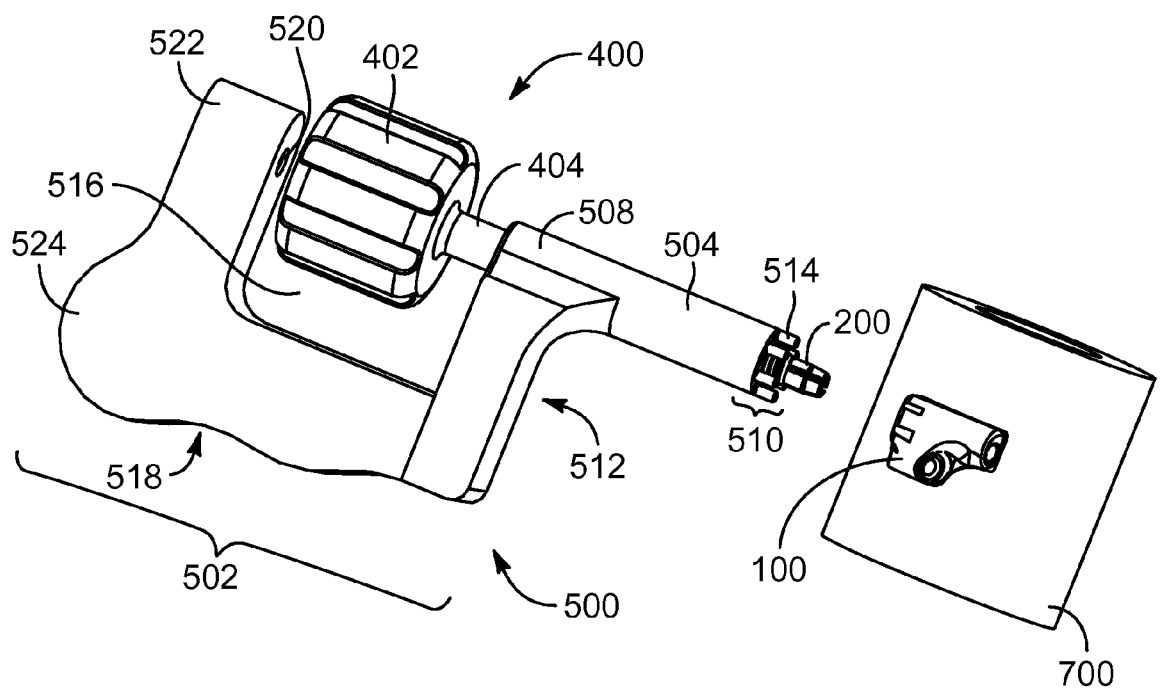
FIG. 23 illustrates a perspective view of a bone fixation instrument assembly, collet and bone fixation element of FIG. 1, the collet engaged with the collet driver.

Referring to FIG. 23, the collet 200 is attached to the collet driver 400 at the collet engagement surface 408 (not shown in this figure). The collet 200 is in an open position allowing for slidable insertion of the cable through the collet 200 through the collet driver 400 and through the second arm bore 520.

It will be appreciated that the bone fixation system is capable of performing to secure a collet without the counter torque instrument 500. Counter torque may be provided by any means known in the art. Without the counter torque instrument 500 a tensioner would be coupled to the collet driver 400 to provide tension to the flexible line 800.

The present invention may be embodied in other specific forms without departing from its spirit or essential characteristics. For example, above are described various alternative examples of bone fixation elements for providing cerclage attachment of bone fragments or bone to prosthesis. It is appreciated that various features of the above-described examples can be mixed and matched to form a variety of other combinations and alternatives. It is also appreciated that this system should not be limited to bone fragments or bone to prosthesis. This bone fixation system may also be used to attach any soft tissue to bone or soft tissue to soft tissue. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for stabilization of a fractured bone, the system comprising:
   a bone fixation element comprising a body having a first end and a second end, the body comprising a first passageway and a second passageway, the first passageway extending between the first end and the second end, the second passageway extending between the first end and the second end, the second passageway decreasing in diameter from the second end to the first end;
   a first collet comprising a proximal portion, a distal portion comprising at least one slit, and a central bore; the first collet further comprising a first engaged position wherein the first collet is positioned at least partially within the first passageway;
   a second collet; and
   a flexible line comprising a first working portion and a second working portion connected to the first working portion, the first working portion comprising a first extended position wherein the first working portion is routed through the central bore; the second working portion attached to the body in a fixed position relative to the second passageway;

wherein the distal portion of the first collet circumferentially engages the first working portion of the flexible line when the first collet is in the first position and the first working portion is in the first extended position, such that the first working portion of the flexible line is held in a fixed position relative to the first passageway;

wherein the second collet is positioned in the second passageway such that the second collet advances toward the first end to reach a first engaged position of the second collet, wherein in response to advancement toward the first end, the decreased diameter of the first end compresses the second collet to cause the second collet to circumferentially engage the second working portion.

2. The system of claim 1, wherein the first passageway comprises a first passageway threaded interface, wherein the proximal portion of the first collet comprises a first collet threaded interface, and wherein the first passageway threaded interface threadably engages the first collet threaded interface when the first collet is in the first engaged position to prevent unintentional withdrawal of the first collet from the first passageway.

3. The system of claim 1, wherein the first passageway decreases in diameter from the first end to the second end, wherein the first collet is positioned in the first passageway such that the first collet advances toward the second end to reach the first engaged position, wherein in response to advancement toward the second end, the decreased diameter of the second end compresses the first collet to cause the first collet to circumferentially engage the first working portion.

4. The system of claim 1, wherein the first collet further comprises ridges, threads or other protrusions at least partially within central bore to enhance engagement between the collet and the first working portion of the flexible line.

5. The system of claim 1, wherein the second working portion is routed through the second passageway, the second working portion comprising a knot positioned to prevent withdrawal of the second working portion through the second passageway.

6. The system of claim 1, further comprising:
a second collet comprising a proximal portion and a distal portion, the second collet further comprising a first engaged position wherein the second collet is positioned at least partially within the second passageway;
wherein the second working portion of the flexible line comprises a first extended position wherein the second working portion is routed through the second collet; and
wherein the distal portion of the second collet circumferentially engages the second working portion of the flexible line when the second collet is in the first engaged position and the second working portion is in the first extended position such that the second working portion of the flexible line is held in the fixed position relative to the second passageway.

7. The system of claim 6, wherein the second passageway comprises a second passageway threaded interface, wherein the proximal portion of the second collet comprises a second collet threaded interface, and wherein the second passageway threaded interface threadably engages the second collet threaded interface when the second collet is in the first engaged position to prevent unintentional withdrawal of the second collet from the second passageway.

8. The system of claim 1, wherein the bone fixation element further comprises a bone interface surface, wherein the bone interface surface is concave.

9. The system of claim 1, wherein the bone fixation element further comprises a bone interface surface, wherein the bone interface surface comprises at least one bone engagement feature protruding from the bone interface surface to restrict sliding of the bone engagement surface against the fractured bone.

10. The system of claim 1, wherein the bone fixation element further comprises at least one slot positioned on the first end of the body to engage at least a portion of an instrument to provide counter torque when positioning the first collet relative to the first passageway.

11. The system of claim 1, wherein the flexible line is a polymer cord.

12. The system of claim 1, wherein the flexible line is radiolucent.

13. The system of claim 1, wherein first collet circumferentially engages the first working portion of the flexible line independently of bending the first working portion of the flexible line.

14. A system for stabilization of a fractured bone, the system comprising:
a bone fixation element comprising a body having a first end and a second end, the body comprising a first passageway and a second passageway, the first passageway extending between the first end and the second end;
a first collet comprising a proximal portion, a distal portion comprising at least one slit, and a central bore; the first collet further comprising a first engaged position wherein the first collet is positioned at least partially within the first passageway;
a second collet comprising a proximal portion and a distal portion, the second collet further comprising a first engaged position wherein the second collet is positioned at least partially within the second passageway; and
a flexible line comprising a first working portion and a second working portion connected to the first working portion, the first working portion comprising a first extended position wherein the first working portion is routed through the central bore; the second working portion attached to the body in a fixed position relative to the second passageway, wherein the second working portion of the flexible line comprises a first extended position wherein the second working portion is routed through the second collet;
wherein the distal portion of the first collet circumferentially engages the first working portion of the flexible line when the first collet is in the first position and the first working portion is in the first extended position, such that the first working portion of the flexible line is held in a fixed position relative to the first passageway;
wherein the distal portion of the second collet circumferentially engages the second working portion of the flexible line when the second collet is in the first engaged position and the second working portion is in the first extended position such that the second working portion of the flexible line is held in the fixed position relative to the second passageway.

15. The system of claim 14, wherein the first passageway comprises a first passageway threaded interface, wherein the proximal portion of the first collet comprises a first collet threaded interface, and wherein the first passageway threaded interface threadably engages the first collet threaded interface when the first collet is in the first engaged position to prevent unintentional withdrawal of the first collet from the first passageway.

16. The system of claim 14, wherein the first passageway decreases in diameter from the first end to the second end, wherein the first collet is positioned in the first passageway such that the first collet advances toward the second end to reach the first engaged position, wherein in response to advancement toward the second end, the decreased diameter of the second end compresses the first collet to cause the first collet to circumferentially engage the first working portion.

17. The system of claim 14, wherein the first collet further comprises ridges, threads or other protrusions at least partially within central bore to enhance engagement between the collet and the first working portion of the flexible line.

18. The system of claim 14, wherein the second working portion is routed through the second passageway, the second working portion comprising a knot positioned to prevent withdrawal of the second working portion through the second passageway.

19. The system of claim 14, wherein the second passageway comprises a second passageway threaded interface, wherein the proximal portion of the second collet comprises a second collet threaded interface, and wherein the second passageway threaded interface threadably engages the second collet threaded interface when the second collet is in the first engaged position to prevent unintentional withdrawal of the second collet from the second passageway.

20. The system of claim 14, wherein the second passageway extends between the first end and the second end, the second passageway decreasing in diameter from the second end to the first end, wherein the second collet is positioned in the second passageway such that the second collet advances toward the first end to reach the first engaged position, wherein in response to advancement toward the first end, the decreased diameter of the first end compresses the second collet to cause the second collet to circumferentially engage the second working portion.

21. The system of claim 14, wherein the bone fixation element further comprises a bone interface surface, wherein the bone interface surface is concave.

22. The system of claim 14, wherein the bone fixation element further comprises a bone interface surface, wherein the bone interface surface comprises at least one bone engagement feature protruding from the bone interface surface to restrict sliding of the bone engagement surface against the fractured bone.

23. The system of claim 14, wherein the bone fixation element further comprises at least one slot positioned on the first end of the body to engage at least a portion of an instrument to provide counter torque when positioning the first collet relative to the first passageway.

24. The system of claim 14, wherein the flexible line is a polymer cord.

25. The system of claim 14, wherein the flexible line is radiolucent.

26. The system of claim 14, wherein first collet circumferentially engages the first working portion of the flexible line independently of bending the first working portion of the flexible line.

27. A system for stabilization of a fractured bone, the system comprising:
a bone fixation element assembly comprising: a body having a first passageway; a first collet; and a flexible line having a first working portion and a second working portion, the first working portion routed through the collet, wherein the second working portion is secured to the body such that the flexible line is routed around the fractured bone; and
a bone fixation instrument assembly comprising a collet driver, the collet driver comprising a proximal handle portion, a distal portion comprising a collet engagement interface shaped to engage the first collet, and a collet driver shaft extending between the proximal handle portion and the distal portion, the bone fixation instrument assembly further comprising a counter torque instrument comprising a counter torque handle and a counter torque shaft positioned distal to the counter torque handle, the counter torque shaft comprising an outer wall defining a shaft bore, a proximal portion, and a distal portion defining a key, wherein the key is shaped to selectively engage the body of the bone fixation element to provide counter torque when the first collet is engaged by the collet driver, wherein the counter torque handle comprises a first arm coupled to the proximal portion of the counter torque shaft and extending non-parallel relative to the counter torque shaft, wherein the counter torque handle further comprises a second arm connected to the first arm, the second arm comprising a second arm bore coaxial with the shaft bore, wherein the counter torque instrument further comprises a notch formed between the second arm bore and the shaft bore, wherein the proximal handle portion of the collet driver is positioned within the notch and coaxial with the second arm bore and the shaft bore;
wherein upon engagement of the first collet by the collet driver, the first collet is advanceable to a first position at least partially within the first passageway in which the first collet circumferentially engages the first working portion of the flexible line to hold the first working portion of the flexible line in a fixed position relative to the body.

28. A system as in claim 27, the collet driver further comprising a collet driver bore extending longitudinally through the collet driver, the flexible line routed through the collet driver bore and the second arm bore.

29. A system as in claim 28, further comprising:
a tensioner attached to the counter torque instrument, wherein the flexible line is further routed through the tensioner, wherein the tensioner is actuable to engage the flexible line to provide tension control to the flexible line.

30. A system as in claim 3, wherein the key comprises at least one prong extending longitudinally from a distal end of the counter torque shaft.

\* \* \* \* \*

UNITED STATES PATENT AND TRADEMARK OFFICE
CERTIFICATE OF CORRECTION

PATENT NO. : 8,241,288 B2  
APPLICATION NO. : 12/341326  
DATED : August 14, 2012  
INVENTOR(S) : Daniel F. Justin et al.

Page 1 of 1

It is certified that error appears in the above-identified patent and that said Letters Patent is hereby corrected as shown below:

In the Claims

Column 12; Line 55; Claim 30: Change "in claim 3" to "in claim 27".

Signed and Sealed this  
Sixteenth Day of July, 2013

Teresa Stanek Rea  
*Acting Director of the United States Patent and Trademark Office*